United States Patent
Smith et al.

(10) Patent No.: US 10,143,199 B2
(45) Date of Patent: *Dec. 4, 2018

(54) METHOD OF KILLING BEDBUG EGGS

(71) Applicant: Ecolab USA Inc., St. Paul, MN (US)

(72) Inventors: Kim R. Smith, Woodbury, MN (US); Erik Olson, Savage, MN (US); Yvonne Killeen, South St. Paul, MN (US); Victor Man, St. Paul, MN (US); Joelle Olson, Shoreview, MN (US); Erin Loosbrock, Eagan, MN (US)

(73) Assignee: Ecolab USA Inc., St. Paul, MN (US)

( * ) Notice: Subject to any disclaimer, the term of this patent is extended or adjusted under 35 U.S.C. 154(b) by 267 days.

This patent is subject to a terminal disclaimer.

(21) Appl. No.: 13/682,320

(22) Filed: Nov. 20, 2012

(65) Prior Publication Data

US 2014/0140948 A1    May 22, 2014

(51) Int. Cl.
*A01N 41/04* (2006.01)

(52) U.S. Cl.
CPC .................................... *A01N 41/04* (2013.01)

(58) Field of Classification Search
CPC ...................................................... A01N 41/04
See application file for complete search history.

(56) References Cited

U.S. PATENT DOCUMENTS

| | | | |
|---|---|---|---|
| 6,814,956 B2 | 11/2004 | Besser et al. | |
| 9,743,661 B2 * | 8/2017 | Smith | A01N 31/02 |
| 2003/0035852 A1 * | 2/2003 | Pullen | 424/736 |
| 2007/0254907 A1 | 11/2007 | Bowles | |
| 2008/0269177 A1 | 10/2008 | Bessette | |
| 2008/0319029 A1 | 12/2008 | Richman et al. | |
| 2009/0223115 A1 | 9/2009 | Lang et al. | |

FOREIGN PATENT DOCUMENTS

| | | | |
|---|---|---|---|
| WO | WO2009/047584 A1 | | 4/2009 |
| WO | WO 2011005325 A1 * | | 1/2011 |

OTHER PUBLICATIONS

Singh et al, "Toxicity of Ionic and Nonionic Surfactants to Six Macrobes Found in Agra, India," Bulletin of Environmental Contamination and Toxicology, vol. 69, No. 2, pp. 265-270 (2002).*
Merriam-Webster, "rinse," verb, Dictionary, available online at http://www.merriam-webster.com/dictionary/rinse and accessed on Jul. 13, 2015 (3 total pages).*
Oxford English Dictionary, "rinse, v.," Oxford University Press, available online at http://www.oed.com/view/Entry/166159?rskey=bGnVzy&result=2&isAdvanced=false&print and accessed on Jul. 13, 2015 (10 total pages).*
Naylor et al, "Practical Solutions for Treating Laundry Infested With Cimex lectularius (*Hemiptera: cimicidae*)," Journal of Economic Entomology, vol. 103, No. 1, pp. 136-139 (2010).*
Pest Management Professional, *The Business of Bed Bugs*, Michael F. Potter, Jan. 1, 2008 (8 pages).
www.bed-bug.net, Bed Bug Killer/How to Kill Bed Bugs/Bed Bug Information, printed Apr. 13, 2010 (1 page).
Bayer Environmental Science, Need to Know, *Temprid® SC now labeled for Bed Bugs*, vol. 7, No. 1, Feb. 18, 2010.
Penn State University, Dept of Entomology, Entomological Notes, Bed Bugs, http://ento.psu.edu/extension/factsheets/bedbugs, printed Apr. 13, 2010 (4 pages).
MGK® Product Code 027911, Material Safety Data Sheet, Bedlam™ Insecticide, Feb. 28, 2006 (2 pages).
TARR Status Report, http://tarr.uspto.gov/, U.S. Appl. No. 77/771,410, Registration No. 3751703, mark:Bedlam Insecticide, printed Apr. 12, 2010 (2 pages).
National Center for Healthy Housing, *What's Working for Bed Bug Control in Multifamily Housing: Reconciling best practices with research and the realities of implementation*, undated (3 pages cover page, table of contents, and p. 22).
FMC Corporation, *Best Management Practices*, Bed Bugs, 2009 (3 pages).
Snell, Eric J., Smith, Todd, Sexton, Wally, *Eclosion of Bed Bug (Cimex lectularius) Eggs after Exposure to Various Compounds*, Snell Scientifics LLC, Meansville, GA, submitted paper at the National Conference on Urban Entomology in Tulsa, OK, May 18-21, 2008 (1 page).

* cited by examiner

*Primary Examiner* — Dennis J Parad
(74) *Attorney, Agent, or Firm* — Merchant & Gould P.C.

(57) ABSTRACT

The present invention relates to a method of pre-rinsing laundry and treating other surfaces employing a composition that can kill bedbug eggs. The composition includes an anionic compound and is at pH just above neutral, e.g., about 7 to about 9.

6 Claims, No Drawings

METHOD OF KILLING BEDBUG EGGS

FIELD OF THE INVENTION

The present invention relates to a method of pre-rinsing laundry and treating other surfaces employing a composition that can kill bedbug eggs. The composition includes an anionic compound and is at pH just above neutral, e.g., about 7 to about 9.

BACKGROUND OF THE INVENTION

The occurrence of bedbugs or other insect pests in textiles or surfaces in areas occupied by people has increased recently. And, such removal of such pests may require pesticides of undesirable toxicity. Bedbugs are relatively small insects, approximately ¼ inch long and less than ¼ inch wide that feed on the blood of animals, including humans. And, their eggs are even smaller, about the size of a dust spec. When first laid, the eggs are sticky causing them to adhere to surfaces. Thus, they can be difficult to find in and on textiles (e.g., laundry).

Some believe that exposing textiles (e.g., laundry) to the heat of drying in a laundry dryer is sufficient to kill bedbugs and bedbug eggs in the textiles. However, due to uneven heat, too short exposure to the heat, and other factors, bedbugs and bedbug eggs often survive a trip through the dryer. Thus, there remains a need for additional methods and compositions for reducing the population of, killing, or reducing the viability of bedbugs and their eggs.

SUMMARY OF THE INVENTION

The present invention relates to a method of pre-rinsing laundry and treating other surfaces employing a composition that can kill bedbug eggs. The composition includes an anionic compound and is at pH just above neutral, e.g., about 7 to about 9.

The present invention includes a method of pre-rinsing a textile suspected of contamination with a pest, such as a bedbug or bedbug egg. This method includes providing the textile suspected of contamination with a pest; pre-rinsing the textile with a composition comprising an effective pesticidal amount of an alcohol sulfate, an alkyl sulfonate, an arylalkyl sulfonate, a salt of a fatty carboxylic acid, a polycarboxylate polymer, or a mixture thereof at a pH of about 7 to about 9. This composition is effective for reducing the viable population of bed bug eggs. The method can also include washing the textile.

The present invention includes a method of treating an article suspected of contamination with a pest. This method includes providing the article suspected of contamination with a pest and applying to the article a composition comprising an effective pesticidal amount of an alcohol sulfate, an alkyl sulfonate, an arylalkyl sulfonate, a salt of a fatty carboxylic acid, a polycarboxylate polymer, or a mixture thereof at a pH of about 7 to about 9. This composition is effective for reducing the viable population of bed bug eggs.

DETAILED DESCRIPTION OF THE INVENTION

The present invention relates to a method of pre-rinsing laundry and treating other surfaces employing a composition that can kill bedbug eggs. The composition includes an anionic compound and is at pH just above neutral, e.g., about 7 to about 9.

The present invention relates to methods employing anionic compounds at near neutral pH as a safe and effective bedbug treatment, for example, in a textile (e.g., laundry) pre-rinse before use of detergent to wash the textile (e.g., laundry). The present pesticidal composition can be drained from the washing machine before the detergent is added. The present method is effective against bedbug eggs.

In an embodiment, the present invention includes a method of pre-rinsing a textile suspected of contamination with a pest, such as a bedbug or bedbug egg. This method can include providing the textile suspected of contamination with a pest. This method can also include pre-rinsing the textile with a composition comprising an effective pesticidal amount of an alcohol sulfate, an alkyl sulfonate, an arylalkyl sulfonate, a salt of a fatty carboxylic acid, a polycarboxylate polymer, or a mixture thereof at a pH of about 7 to about 9. This composition is effective for reducing the viable population of (e.g., killing) bed bug eggs. The method can also include washing the textile.

Textiles that can be treated with the method of the invention include, for example, clothing, bedding, a drape, a towel, a mattress, upholstery, or a combination thereof.

Suitable anionic compounds include alcohol sulfates, alkyl sulfonates, salts of fatty carboxylic acids, and non-surface active polycarboxylated polymers. In an embodiment, suitable anionic compounds include alcohol sulfates, alkyl sulfonates, and non-surface active polycarboxylated polymers. Suitable fatty alcohol sulfates include a $C_8$-$C_{18}$ aliphatic alcohol, for example, a linear aliphatic alcohol. In an embodiment, the composition employed in the present method does not include an alcohol ethoxylate, for example, when the composition includes a fatty alcohol sulfate. Suitable surface-active sulfonates include a $C_8$ to $C_{18}$ alkyl sulfonate. Suitable anionic compounds include a $C_8$ to $C_{18}$ arylalkyl sulfonates, such as sodium dodecylbenzene sulfonate. Suitable fatty carboxylic acid salts include C8 to C24 carboxylic acids with an alkali metal cation (e.g., potassium, sodium, or lithium). Suitable pH include 7 to 9, 7 to 8, and 7.5 to 8.5.

Suitable non-surface active polycarboxylate polymers include a polyacrylate or polymethacylate or copolymers thereof, maleic/olefinic copolymer, acrylate/olefinic copolymer, or mixtures thereof. In an embodiment the polymer includes an acrylic/maleic copolymer. The molecular weight of the polymer can be, for example, about 1,000 to about 10,000, about 2000 to about 5000, or about 3000 to about 4000.

In an embodiment, the effective pesticidal amount of anionic compound is about 0.1 wt-% to about 3 wt-%.

In an embodiment, the composition also includes water and, optionally, fragrance, dye, or both fragrance and dye.

In an embodiment, the composition is pesticidal against cockroach, bed bug, bed bug egg, ant, fly, termite, or mixture thereof.

The present invention also includes a method of treating an article suspected of contamination with a pest, such as a bedbug or bedbug egg. This method can include providing the article suspected of contamination with a pest. This method can include applying to the article a composition comprising an effective pesticidal amount of an alcohol sulfate, an alkyl sulfonate, an arylalkyl sulfonate, a salt of a fatty carboxylic acid, a polycarboxylate polymer, or a mixture thereof at a pH of about 7 to about 9. This composition is effective for reducing the viable population of bed bug eggs. Suitable articles include, for example, a hard surface selected from the group consisting of a floor, a ceiling, a window, a wall, and a combination thereof.

Anionic Compounds

The present composition can include an anionic surfactant as an anionic compound. Suitable anionic surfactants include organic sulfonate surfactant, organic sulfate surfactant, carboxylate surfactant, mixtures thereof, or the like. In an embodiment, the anionic surfactant includes alkyl sulfonate, alkylaryl sulfonate, alkylated diphenyl oxide disulfonate, alkylated naphthalene sulfonate, alcohol alkoxylate carboxylate, alkanoic ester, sulfuric acid ester, salt or acid form thereof, or mixture thereof. The particular salts will be suitably selected depending upon the particular formulation and the needs therein.

Suitable anionic surfactants include sulfonic acids (and salts), such as isethionates (e.g. acyl isethionates), alkylaryl sulfonic acids and salts thereof, alkyl sulfonates, and the like.

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives or their free acids. Suitable sulfonates include olefin sulfonates, such as long chain alkene sulfonates, long chain hydroxyalkane sulfonates or mixtures of alkenesulfonates and hydroxyalkane-sulfonates.

In certain embodiments, the present compositions including an anionic surfactant, such as a normal C8 sulfonate, can be non-foam or low foam compositions. Such compositions can be advantageous for applications such as clean in place, machine warewashing, destaining, and sanitizing, laundry washing, destaining, and sanitizing, etc.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present.

Suitable anionic surfactants include alkyl or alkylaryl ethoxy carboxylates of Formula 3:

$$R\text{—}O\text{—}(CH_2CH_2O)_n(CH_2)_m\text{—}CO_2X \quad (3)$$

in which R is a $C_8$ to $C_{22}$ alkyl group or

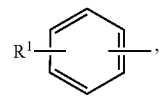

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In an embodiment, in Formula 3, n is an integer of 4 to 10 and m is 1. In an embodiment, in Formula 3, R is a $C_8$-$C_{16}$ alkyl group. In an embodiment, in Formula 3, R is a $C_{12}$-$C_{14}$ alkyl group, n is 4, and m is 1.

In an embodiment, in Formula 3, R is

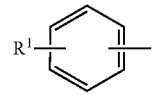

and $R^1$ is a $C_6$-$C_{12}$ alkyl group. In an embodiment, in Formula 3, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12\text{-}13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

The present invention may be better understood with reference to the following examples. These examples are intended to be representative of specific embodiments of the invention, and are not intended as limiting the scope of the invention.

EXAMPLES

Example 1

Treating Bedbug Eggs with Fatty Alcohol Sulfate at pH 9 to 10

Bedbug eggs on a substrate were exposed to a 100° F. test composition for 5 minutes and then examined. A 1% solution of sodium lauryl sulfate at a pH of 9 to 10 did not kill bedbug eggs. Water by itself killed about 20% of the bedbug eggs. And, complete kill was accomplished by a commercial bedbug killer sold under the tradename Transport.

Example 2

Treating Bedbug Eggs with Anionic Compounds Near Neutral pH

Aqueous test compositions of each of several anionic compounds prepared and adjusted to near neutral pH of about 7-8. Bedbug eggs were then contacted with a 100° F. test composition for 5 min.

| Test Composition (pH 7-8) | % Kill of Bedbug Eggs | % Kill of Bedbug Eggs and Nymphs |
| --- | --- | --- |
| Control | 100 | 100 |
| 1% decanol, 5% Surfonic 12-6 | | |
| 1% sodium octyl sulfonate | 90 | 95 |
| 1% sodium lauryl sulfate | 75 | 100 |
| 1% sodium cocoate | 70 | 90 |
| 1% Acusol 448 | 80 | 95 |
| 1% sodium dodecylbenzene sulfonate | 30 | 30 |
| 0.1% sodium lauryl sulfate | 70 | 95 |
| 1% sodium lauryl ether sulfate | 35 | 35 |

Surfonic 12-6 is a decyl/lauryl alcohol ethoxylate with 6 EO available from Huntsman Chemical. Acumer 448 is an acrylic/maleic copolymer available from Rohm & Haas (Dow), having a molecular weight of about 3000-4000.

As used herein, weight percent (wt-%), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A method of treating bedding suspected of contamination with bed bug eggs, the method consisting of:
   applying a bedbug treatment composition to the bedding in a washing machine, the bedbug treatment composition consisting of water, from about 0.1 to about 3% C8-C18 alkyl sulfonate; and optionally one or more fragrances and dyes, wherein the composition has a pH above 7.5 and below about 9;
   wherein the bedbug treatment composition is effective for reducing the viable population of bed bug eggs;
   draining and removing the bedbug treatment composition from the washing machine; and
   after draining, applying a laundry detergent and water to the bedding in the washing machine and washing the bedding.

2. The method of claim 1, wherein the alkyl sulfonate is sodium lauryl sulfonate or sodium dodecylbenzene sulfonate.

3. The method of claim 1, wherein the alkyl sulfonate is an aromatic alkyl sulfonate.

4. The method of claim 1, wherein the step of applying a bedbug treatment composition has a duration of about 5 min.

5. The method of claim 1, wherein the solution has a temperature of about 100 ° F.

6. The method of claim 5, wherein the viable population of bed bug eggs is reduced by at least 70%.

* * * * *